(12) United States Patent
Alferiev et al.

(10) Patent No.: US 9,233,163 B2
(45) Date of Patent: Jan. 12, 2016

(54) HYDROLYTICALLY RELEASABLE PRODRUGS FOR SUSTAINED RELEASE NANOPARTICLE FORMULATIONS

(75) Inventors: Ivan Alferiev, Clementon, NJ (US); Michael Chorny, Huntingdon Valley, PA (US); Robert J. Levy, Merion Station, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 102 days.

(21) Appl. No.: 13/976,776

(22) PCT Filed: Dec. 28, 2011

(86) PCT No.: PCT/US2011/067531
§ 371 (c)(1),
(2), (4) Date: Jul. 23, 2013

(87) PCT Pub. No.: WO2012/092339
PCT Pub. Date: Jul. 5, 2012

(65) Prior Publication Data
US 2013/0296285 A1 Nov. 7, 2013

Related U.S. Application Data

(60) Provisional application No. 61/427,615, filed on Dec. 28, 2010.

(51) Int. Cl.
*A61K 47/48* (2006.01)
*C08B 37/02* (2006.01)

(52) U.S. Cl.
CPC ..... *A61K 47/48123* (2013.01); *A61K 47/48107* (2013.01); *A61K 47/48315* (2013.01); *C08B 37/0021* (2013.01)

(58) Field of Classification Search
None
See application file for complete search history.

(56) References Cited

U.S. PATENT DOCUMENTS

| | | | |
|---|---|---|---|
| 7,175,909 B2 | 2/2007 | Hu et al. | |
| 7,175,912 B2 | 2/2007 | Cui et al. | |
| 7,635,734 B2 | 12/2009 | Alferiev et al. | |
| 2004/0077595 A1 | 4/2004 | Cheng et al. | |
| 2005/0271745 A1 | 12/2005 | Gruettner et al. | |
| 2006/0003976 A1 | 1/2006 | Zhang et al. | |
| 2006/0041182 A1* | 2/2006 | Forbes et al. | A61F 2/82 600/12 |
| 2009/0082611 A1 | 3/2009 | Levy et al. | |
| 2009/0216320 A1 | 8/2009 | Levy et al. | |
| 2010/0305149 A1* | 12/2010 | Yurkovetskiy et al. | 514/283 |

FOREIGN PATENT DOCUMENTS

CN 1743337 A 3/2006

OTHER PUBLICATIONS

Kagoshima et al., in Bioorganic & Medicinal Chemistry Letters 19, 3559-3563 (2009).*
Chorny et al. in Circulation; 2008;118:S_960-S_961 (Abstract 4922).*
Muller et al., Nanosuspensions as particulate drug formulations in therapy rationale for development and what we can expect for the future, Advanced Drug Reviews vol. 47, (2001), pp. 3-19.
Sarkar, Engineering of Nanoemulsions for Drug Delivery, Current Drug Delivery, 2005 , vol. 2, pp. 297-310.
Manjunath et al., Solid Lipid Nanoparticles as Drug Delivery Systems, Methods Find Exp Clin Pharrnacol, 2005, vol. 27(2), pp. 127-144.
Stevens et al., A Folage Receptor-Targeted Lipid Nanoparticle Formulation for a Lipophilic Paclitaxel Prodrug, Pharmaceutical Research, vol. 21, No. 12, Dec. 2004, pp. 2153-2157.
Reddy et al., Macromolecular Anticancer Therapeutics (Google eBook), 2010, p. 315.
Phillip James Stevens, B.S., Dissertation "An Approach to Drug Formulation and Targeting *Liposomes and Lipid Nanoparticles for Folate Receptor Targeting*", 2005.
International Search Report dated Jul. 11, 2013, for Int'l Appl. No. PCT/US2011/067531, filed Dec. 28, 2011.

* cited by examiner

*Primary Examiner* — Dennis Heyer
(74) *Attorney, Agent, or Firm* — RatnerPrestia

(57) ABSTRACT

A prodrug according to formula (I) wherein $R^2$ is a residue of a drug, said drug having a hydroxyl group by which the $COOR^2$ group is formed; Z is O or NH; m is 0 or 1; and $R^3$ is an organic moiety comprising a lipophilic group or a residue of a polymer, provided that Z is 0 if the polymer is carboxymethyl dextran. A system includes a plurality of magnetic nanoparticles including a prodrug as described above, a stent and a source of uniform magnetic field capable of producing temporary magnetization of the stent and/or the magnetic nanoparticles. A method of treating a medical condition with a drug includes administering to a patient in need of the drug a prodrug as described above, the prodrug being capable of releasing the drug in the patient after the administration step.

4 Claims, 6 Drawing Sheets

HYDROLYTICALLY RELEASABLE PRODRUGS FOR SUSTAINED RELEASE NANOPARTICLE FORMULATIONS

This application is the national phase filing of International Application No. PCT/US2011/067531, filed 28 Dec. 2011, and claims priority of U.S. Provisional Application No. 61/427,615, filed 28 Dec. 2010, the entireties of which applications are incorporated herein by reference for all purposes.

BACKGROUND

The inventors have previously disclosed magnetic targeting of iron oxide-containing, magnetically responsive nanoparticles (MNP) to stents in vivo, demonstrating the suitability of this approach for delivering drugs, gene vectors and cell therapy. Nanoparticle formulations can potentially offer several important advantages, including delivery of poorly water soluble drugs in a form suitable for parenteral administration, protection of chemically labile therapeutic agents from degradation, ability to control the biodistribution and fate of the agent in the body, and controlled drug release at the site of disease.

Paclitaxel (PTX) is a potent antiproliferative drug that binds to β-tubulin and promotes the assembly of abnormally stable microtubules, thereby preventing normal cell division. The inventors have previously disclosed a significant antirestenotic effect of a PTX-loaded MNP formulation that can be magnetically targeted to arterial or other sites in a patient. Further advances in methods of delivering MNP or other nanoparticles loaded with PTX or other therapeutic agents to a patient would be a welcome contribution to the art.

Various publications, including patents, published patent applications and scholarly articles, are cited throughout the specification. Each of these publications is incorporated by reference herein, in its entirety.

SUMMARY

In one aspect, the invention provides a prodrug according to formula (I)

(I)

wherein $R^2$ is a residue of a drug, said drug having a hydroxyl group by which the $COOR^2$ group is formed; Z is O or NH; m is 0 or 1; and $R^3$ is an organic moiety comprising a lipophilic group or a residue of a polymer, provided that Z is O if the polymer is carboxymethyl dextran.

In another aspect, the invention provides a system including a plurality of magnetic nanoparticles including the prodrug as described above, a stent and a source of uniform magnetic field capable of producing temporary magnetization of the stent and/or the magnetic nanoparticles.

In yet another aspect, the invention provides a method of treating a medical condition with a drug, including administering to a patient in need of the drug a prodrug as described above, the prodrug being capable of releasing the drug in the patient after the administration step.

As used herein, the term "residue" refers to that portion of a starting material molecule that remains in an indicated product molecule after formation of an indicated ester or amide moiety in that product.

DETAILED DESCRIPTION

Figure 1:
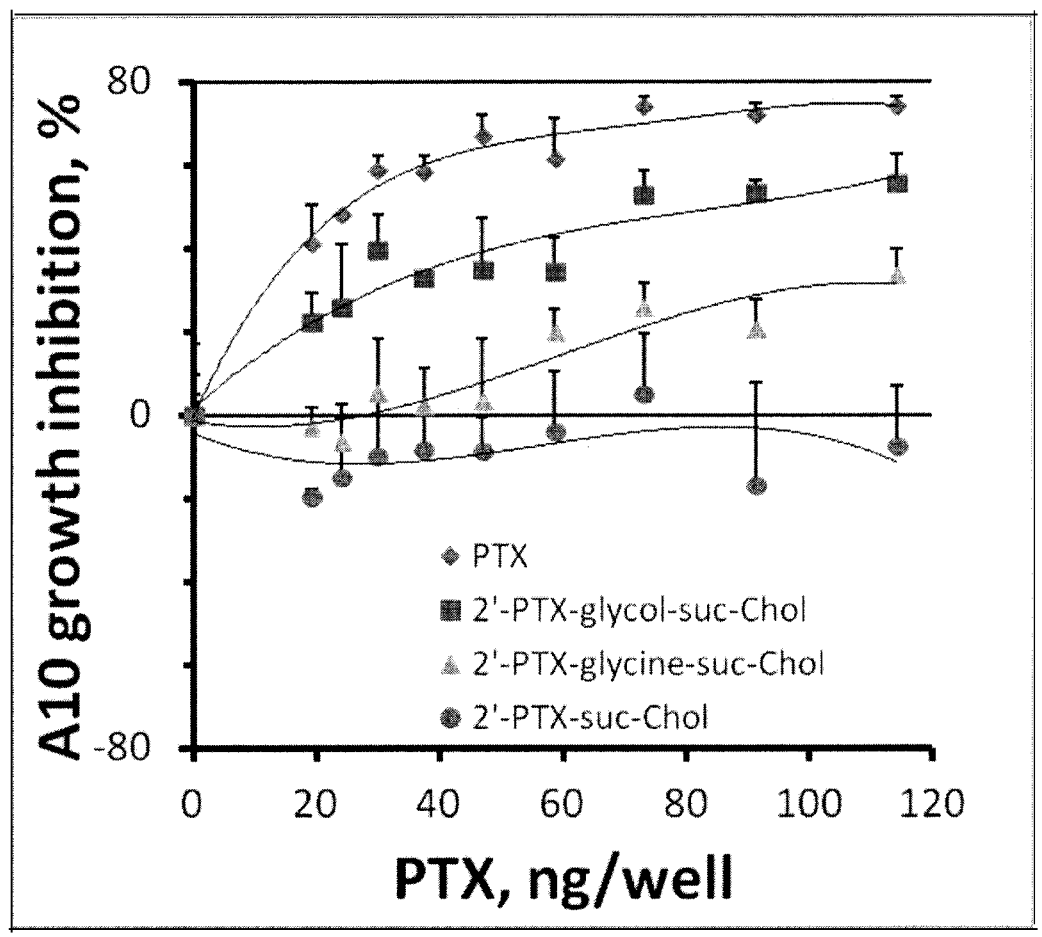
FIG. 1 shows the results of a study of A10 growth inhibition by rapidly cleavable hydrophobic PTX derivatives according to the invention, vs. controls.

It has now been found that the release kinetics of PTX and other drugs from previously described MNP configurations may not be ideally suited for providing maximal therapeutic effect. For example in a typical MNP comprising PTX, iron oxides and a polylactide carrier, about 50% and 80% of the drug is released under sink conditions after 4 hr and 24 hr, respectively. This may be too fast for optimal restenosis inhibition, given that the period of vulnerability to restenotic activity may extend for several weeks. It is believed that the large surface area to volume ratio and small linear dimensions of nanoparticles, combined with the relatively low molecular weight of PTX and limited affinity toward the carrier particles, result in the excessively rapid PTX escape from the nanoparticles. To deal with this problem, it has been found necessary to greatly increase the affinity of the PTX for the polymeric carrier. This has now been done by binding PTX to a structure (hereinafter "anchor") that limits the diffusivity within the MNP compared with that of unbound PTX itself. The resulting PTX-anchor conjugate is a PTX prodrug. Prodrugs according to the invention are converted to the corresponding drugs (e.g., PTX) in vivo in a patient, which may be a human or other animal. The prodrug can be incorporated in the MNP with a high entrapment yield and can provide protracted drug release at the site of arterial injury.

In some embodiments, the anchor is a lipophilic group such as cholesterol or tocopherol, which tend to associate with polylactide (or another polymer) present as a binder in the MNP. Other lipophilic groups or residues may be provided by carboxylic acids, typically those comprising from 8 to 30 carbon atoms, for example certain biologically inert or bioactive fatty acids. Specific examples include palmitic, stearic, oleic, ricinoleic, docosahexaenoic and retinoic acids. In some embodiments of the invention, an anchor is chosen to provide the resulting conjugate with PTX (or other drug) with a log P value of at least 5, or at least 7, or at least 8, or at least 9, wherein log P is the logarithm of the octanol/water partition coefficient.

More generally, prodrugs according to the invention may be described according to formula (I)

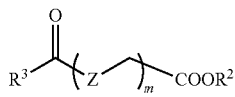

(I)

wherein $R^2$ is a residue of a drug, said drug having a hydroxyl group by which the $COOR^2$ group is formed; Z is O or NH; m is 0 or 1; and $R^3$ is an organic moiety comprising a lipophilic group or a residue of a polymer, provided that Z is O if the polymer is carboxymethyl dextran.

In some embodiments of the invention, $R^3$ consists of the above-mentioned lipophilic group, or $R^3$ is the abovementioned a residue of a polymer. The polymer bears a plurality of carboxyl groups, wherein the $R^3$—CO group in formula (I) is formed from a carboxyl group present on the lipophilic group or from a carboxyl group on the polymer.

In some embodiments of the invention, $R^3$ is a moiety according to formula (II)

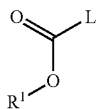

(II)

wherein $R^1$ is said lipophilic group or $R^1$ is a residue of a polymer, wherein the polymer bears a plurality of hydroxyl groups by at least one of which the $R^1$-containing ester group of formula (II) is formed. L is a linking group comprising a linear or branched hydrocarbyl moiety that may optionally comprise in-chain or pendant heteroatom substituents and/or in-chain or pendant unsaturated and/or cyclic/heterocyclic moieties. Nonlimiting examples of in-chain or pendant substituents or moieties include —O—, —S—, —NH—, —NR—, —CO— and —COO—, olefinic and acetylenic groups, where R is an organic moiety. In some embodiments L is $(CH_2)_n$ in which n is an integer in a range from 1 to 20. In typical embodiments, n is 2 or 3 or 4.

In some embodiments of the invention, $R^3$ is a moiety according to formula (III)

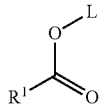

(III)

wherein $R^1$ is the abovementioned lipophilic group or $R^1$ is a residue of a polymer in which the polymer bears a plurality of carboxyl groups. L is as defined above for formula (II), and the $R^1$—CO group in formula (III) is formed from a carboxyl group present on the lipophilic group or is formed from a carboxyl group on the polymer.

Typical lipophilic groups may be biocompatible, although this is not required. Exemplary lipophilic groups include residues of tocopherol, cholesterol, oleic acid, retinoic acid and N-(4-hydroxyphenyl)retinamide. A wide variety of groups are sufficiently lipophilic, and any of these may be used according to the invention. The groups are typically hydrocarbyl groups, optionally comprising in-chain, in-ring or pendant heteroatom substituents and/or cyclic or heterocyclic moieties. In some embodiments, lipophilic groups may be chosen so as to provide additional functionalities to the construct, such as enhanced therapeutic effect or in vivo/in vitro traceability using fluorescent, magnetic resonance or positron emission tomography imaging. Specific examples of lipophilic groups useful for increasing pharmacological activity or enabling imaging relevant for diagnostic or theranostic applications include, but are not limited to, 13-cis-retinoic acid (anticancer agent) and BODIPY FL (fluorescent probe, 4,4-difluoro-5,7-dimethyl-4-bora-3a,4a-diaza-s-indacene-3-propionic acid), respectively.

For example, a prodrug according to the invention in which the moiety of formula (II) is present, and in which L is $CH_2$ or $(CH_2)_2$ and m is 0, may be prepared in which the OOC-L moiety is derived from the biodegradable oxaloacetic or alpha-ketoglutaric acids, respectively. Alternatively, a prodrug in which the moiety of formula (III) is present, and in which L is $(CH_2)_2$ and m is 0, may be prepared in which the O-L moiety is derived from 4-hydroxy-2-oxobutyric acid.

In some embodiments, the anchor is a polymer to which the PTX is linked, which helps retain the PTX in the MNP for longer periods of time than obtained with PTX itself. The polymer will typically be a biodegradable polymer, and in some embodiments of the invention a PTX-conjugated polymer is the only polymer in the MNP, where it also acts as a binder to hold the nanoparticle together.

In some embodiments the PTX is linked to the anchor via an ester at the C2' position of PTX, and hydrolysis of the ester releases PTX. The inventors have further found, however, that the hydrolysis rate of most ester linkages is too slow, and thus significant degradation of the PTX (e.g., through hydrolysis of ester groups in the PTX moiety itself) occurs before the PTX is released, resulting in loss of therapeutic activity. Therefore, the invention provides conjugation via specially designed esters having enhanced hydrolysis rates, providing excellent PTX delivery and cell growth inhibitory activity. This technique can also be applied to other therapeutic agents according to the invention, including for example sirolimus (preferably via ester formation using OH groups either at C28 or at C40) and lestaurtinib (CEP-701).

Conjugates as described above may afford improved drug performance characteristics in controlled release formulations, either magnetic or non-magnetic, employing nanoparticles (i.e., particles having a maximum dimension less that 1 micron). The nanoparticles may include polymer-based nanoparticles (particles in which the prodrug is admixed with a solid or liquid polymer), nanosuspensions (dispersions containing prodrug nanocrystals), nanoemulsions (submicron oil droplets in which the prodrug is dissolved or dispersed), solid lipid nanoparticles (non-polymeric nanoparticles made of lipids solid at room temperature in which the prodrug is dissolved or dispersed), and micelles. Any of these types of nanocarriers can exhibit optimized incorporation yields and release kinetics by increasing drug hydrophobicity through use of prodrugs according to the invention. A number of methods of micelle formation are known in the art, and any of these is suitable for use according to the invention. Formation of nanosuspensions is described for example in the papers cited in Nanosuspensions as particulate drug formulations in therapy: Rationale for development and what we can expect for the future, R. H. Mueller et al., *Advanced Drug Delivery Reviews* 47 (2001) 3-19. Preparation of nanoemulsions is described in Engineering of Nanoemulsions for Drug Delivery, Dipak K. Sarker, *Current Drug Delivery*, 2005, 2, 297-310. Methods of making solid lipid nanoparticles are disclosed in Solid Lipid Nanoparticles as Drug Delivery Systems, K. Manjunath et al., *Methods Find Exp Clin Pharmacol* 2005, 27(2): 127-144.

Any of the above-mentioned ways of formulating prodrugs according to the invention can extend the period of effective drug release and provide safer and more efficient therapies for cardiovascular disease. These formulations may also be used to treat other types of disease. For example, they may be used for targeted cancer treatment by taking advantage of the enhanced permeability and retention (EPR) effect, promoting preferential extravasation and retention of large molecules or nanoparticles with a certain size, typically 10 nm-400 nm, in tumor tissue with leaky vasculature, or alternatively, via magnetic and/or affinity targeting strategies enabled by surface functionalization with appropriate affinity ligands.

In the context of magnetically targeting PTX to a stented site, the use of MNP loaded with a rapidly cleavable PTX-containing prodrug as described above extends the period of PTX release and enables increased retention of the regenerated PTX at the site of injury, translating into a more pronounced antirestenotic effect.

Rapidly Cleavable PTX-Containing Prodrugs

In order to maximize the fraction of functional (i.e., not degraded) PTX regenerated from the prodrug, the invention provides a structure where ester bonds exhibiting exceptionally high rates of hydrolytic cleavage are incorporated between the anchor and PTX. If the anchor has available carboxylic groups, e.g., fatty acids or poly(L-glutamic acid), the linker may consist of a N-acylated glycine or O-acylated glycolic acid residue (See Example 5 below). In the case where the anchor possesses a hydroxyl function available for conjugation, such as that found in cholesterol or tocopherol, the linking group consists of a biocompatible dicarboxylic acid residue (e.g. succinate, as in Examples 1-3 and 6-11) forming either an amide linkage with glycine or an ester linkage with glycolic acid. For cholesterol, exemplary compounds are, respectively, PTX 2'-[N-(3-cholesteryloxycarbonyl)propionyl]glycinate and PTX 2'-(3-cholesteryloxycarbonyl)propionyloxyacetate. Scheme 1 shows these structures, abbreviated as 2'-PTX-glycine-suc-Chol and 2'-PTX-glycol-suc-Chol.

Scheme 1

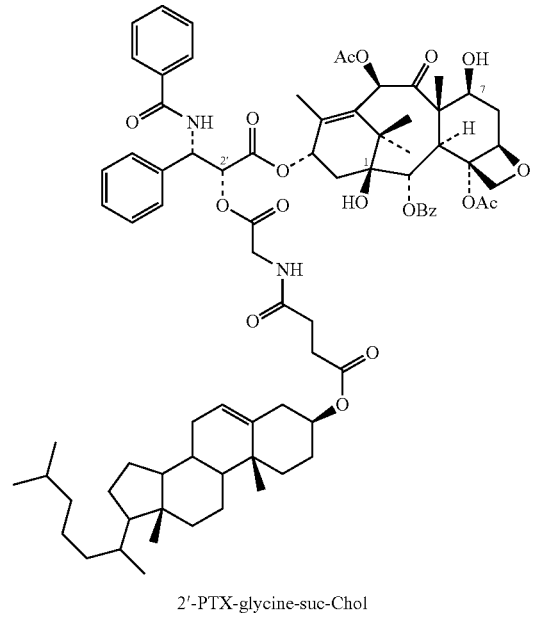

2'-PTX-glycine-suc-Chol

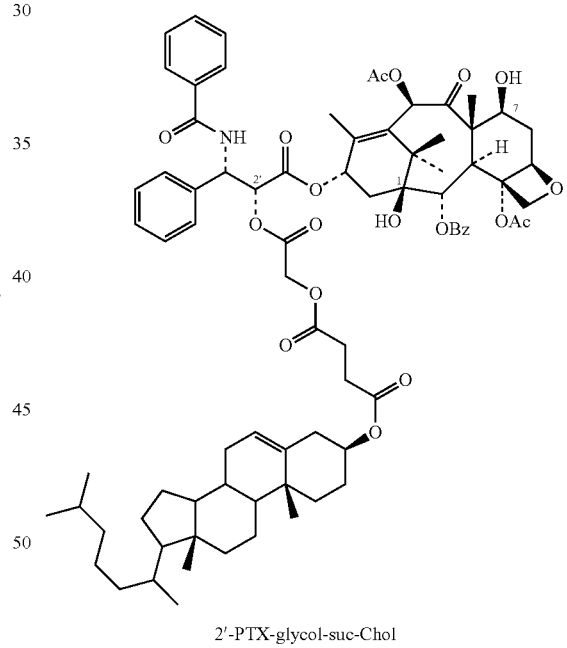

2'-PTX-glycol-suc-Chol

For each of these compounds, the more rapid cleavage of the bridge between PTX and cholesterol in comparison to the ester bonds in the structure of PTX itself ensures that the pharmacological activity of PTX is maximally retained. The rapid hydrolytic cleavage is provided by conjugation between the C2' hydroxyl group of PTX and a carboxylic acid having increased electrophilicity of the carbonyl group: N-(3-cholesteryloxycarbonyl)propionylglycine (1, Scheme 2) or (3-cholesteryloxycarbonyl)propionyloxyacetic acid (2a, Scheme 3).

Scheme 2. Synthesis of N-(3-cholesteryloxycarbonyl)propionylglycine (1)

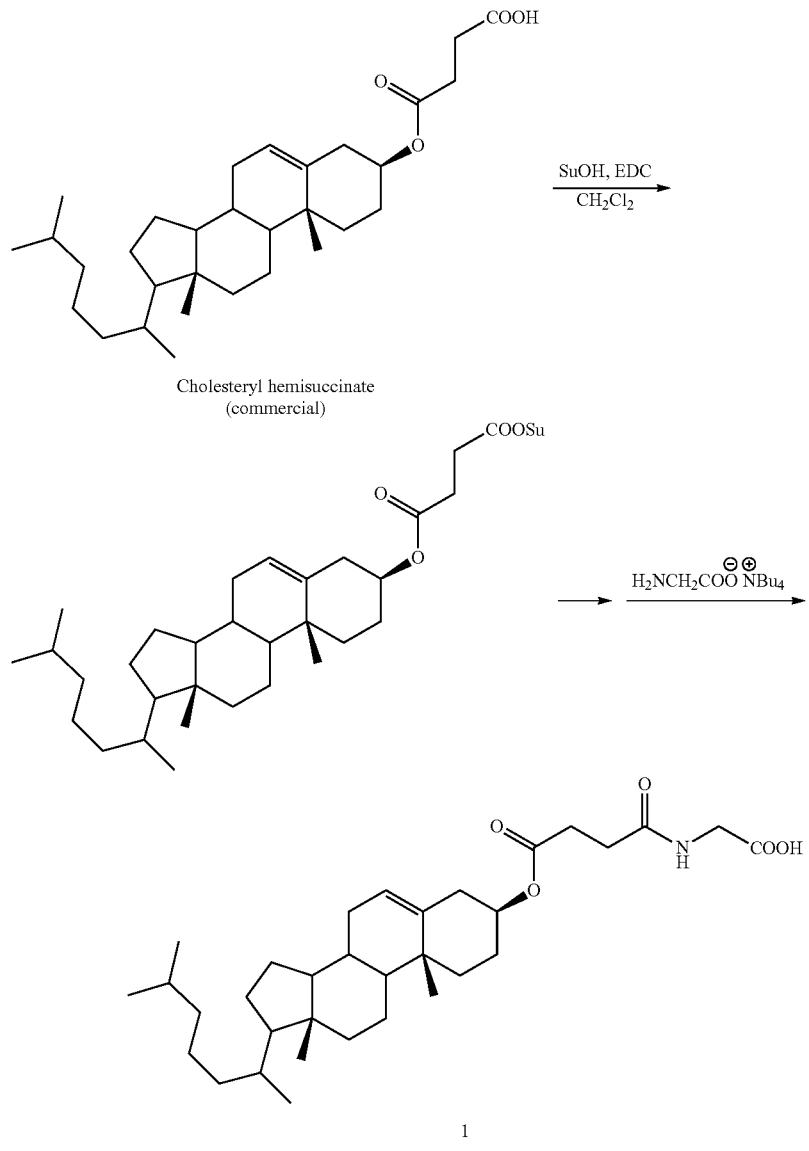

Su = N-succinimidyl

Scheme 3.
Synthesis of acids 2a and 2b

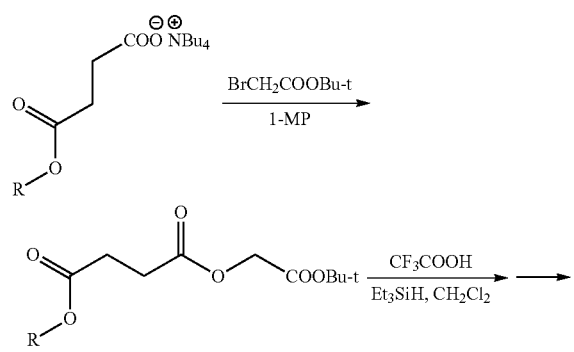

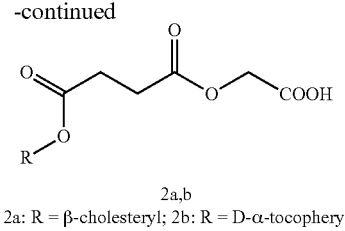

2a: R = β-cholesteryl; 2b: R = D-α-tocopheryl

In other embodiments of the invention, the hydrophobic cholesteryl residue in the acid 2a is replaced with the residue of tocopherol, with the formation of tocopherol-derived acid (2b, Scheme 3), equally suitable for preparation of a labile PTX conjugate (2'-PTX-glycol-suc-Toc, Scheme 4).

Conjugates of PTX with the acids 1 and 2a,b may be prepared by direct coupling of the free acids with PTX using 1-ethyl-3-(3-dimethylaminopropyl)carbodiimide hydrochloride (EDC) as a coupling agent and 4-dimethylaminopyridine tosylate (DPTS) as a catalyst in dichloromethane solution (Scheme 4). The same method is also suitable for the coupling of PTX with cholesteryl hemisuccinate to prepare the PTX conjugate with a regular (i.e., not rapidly hydrolyzable) ester bond (2'-PTX-suc-Chol, Scheme 4), used as a reference compound for comparison with the rapidly cleavable PTX conjugates.

This strategy for providing prodrugs rapidly converted into a parent drug is not limited to PTX, but can also be applied according to the invention to other drugs having a hydroxyl group capable of ester formation. Examples include CEP-701 (lestaurtinib) and CEP-751, a family of structurally related tyrosine kinase inhibitors with a clinical potential as anticancer agents (See Scheme 5 below) and sirolimus, an immunosuppressant drug which is also used clinically as an antirest-

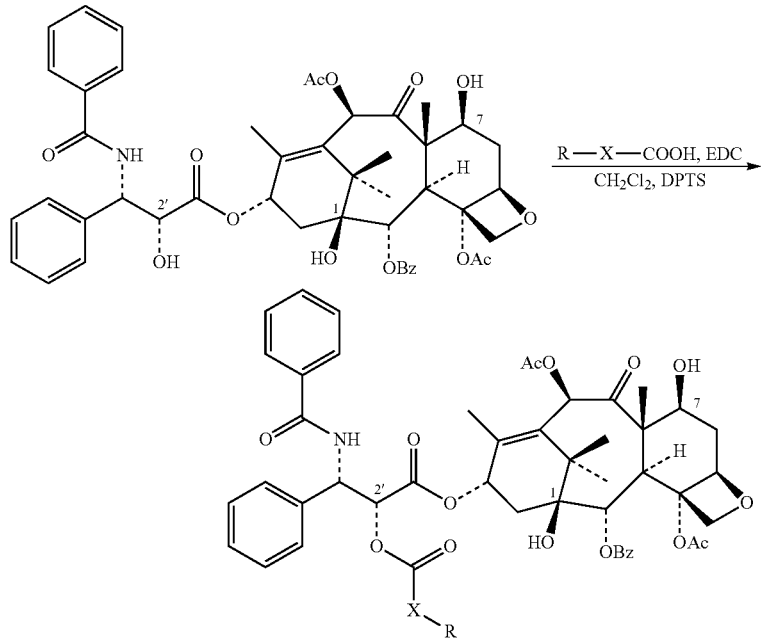

2'-PTX-glycine-suc-Chol: R = β-cholesteryl, X = —O—CO—(CH$_2$)$_2$—CO—NH—CH$_2$—
2'-PTX-glycol-suc-Chol: R = β-cholesteryl, X = —O—CO—(CH$_2$)$_2$—CO—O—CH$_2$—
2'-PTX-glycol-suc-Toc: R = D-α-tocopheryl, X = —O—CO—(CH$_2$)$_2$—CO—O—CH$_2$—
2'-PTX-suc-Chol: R = β-cholesteryl, X = —O—CO—(CH$_2$)$_2$—

Model experiments estimating the stability of ester bonds in ethyl esters of N-acetylglycine (model of PTX conjugate with the acid 1) and acetoxyacetic acid (model of PTX conjugate with the acid 2a) in pH=7 phosphate buffer at 21-22° C. revealed respective times of half-hydrolysis of 27 and 9 days, whereas for ethyl acetate (as a model of a regular ester derivative of PTX) the half-hydrolysis time in the same conditions was approximately 200 days. Based on the results of the model experiments, paclitaxel 2'-esters with N-acylglycines and acyloxyacetic acids containing highly hydrophobic residues (e.g., derived from cholesterol or tocopherol) are the most suitable for encapsulation in sustained release nanoparticle formulations as rapidly cleavable PTX prodrugs. In the context of in-stent restenosis therapy, these unique designs more effectively confine the drug formulated in magnetically targeted MNP to the stented area. Importantly, the by-products of the prodrug degradation deriving from the anchor and the linking group are all biocompatible endogenous small molecules, rapidly eliminated via natural metabolic pathways.

enotic agent. For both of these, esterification is typically at the methylol hydroxyl.

Scheme 5.
Synthesis of cleavable CEP-701 conjugate with the acid 2a
(CEP-glycol-suc-Chol)

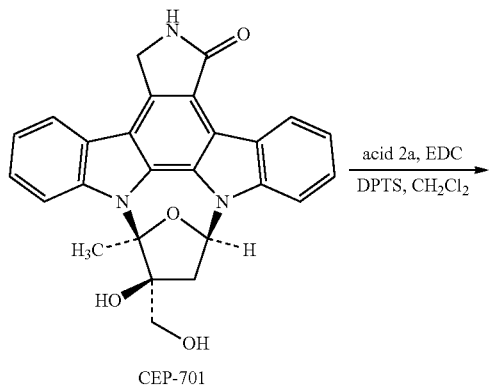

CEP-701

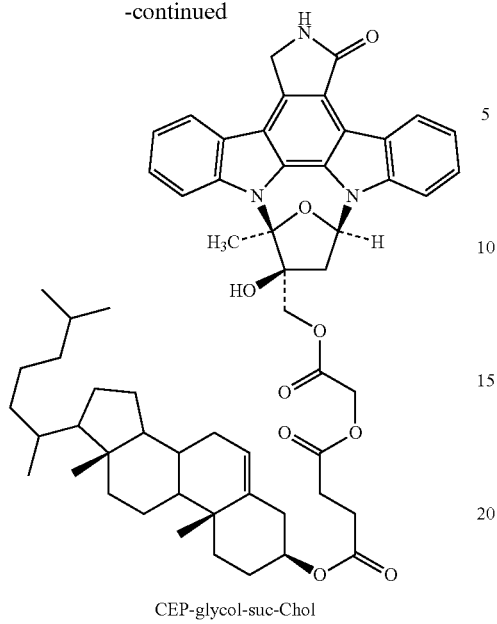

CEP-glycol-suc-Chol

Rapidly Cleavable Codrug Constructs Formed with Retinoic Acid as a Second Pharmacophore In another embodiment, a codrug is formed in which retinoic acid is bound via a rapidly cleavable linkage to another moiety with pharmaceutical activity. Being highly lipophilic and thus providing a highly efficient anchor for constructing drug derivatives with enhanced lipophilicity, retinoic acid and its derivatives also exhibit pharmacological activity highly relevant for treating proliferative diseases, including cancer and restenosis. One example is 13-cis-retinoic acid, an anticancer agent with proven efficacy. It has now been found that such compounds can be used to design codrugs with enhanced therapeutic efficiency due to the additive or synergistic action of the two pharmacophores recovered upon hydrolytic cleavage of the construct.

One exemplary compound is a CEP-glycol-Ret, a conjugate CEP-701 and 13-cis-retinoic acid, prepared in the following manner. 13-cis-Retinoyloxyacetic acid (8) was prepared from 13-cis-retinoic acid according to Scheme 6, as a novel type of lipophilic O-acylated glycolic acid derivative. The procedure was similar to that used above for the acids 2a,b, with modifications (employing 9-fluorenylmethyl protective group instead of tert-butyl).

Scheme 6. Synthesis of 13-cis-retinoyloxyacetic acid 8

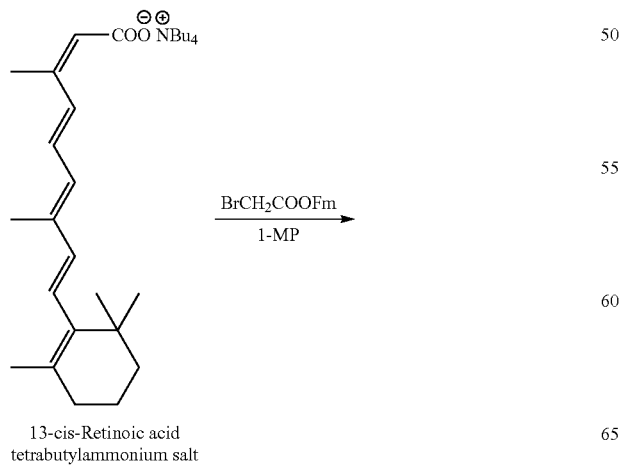

13-cis-Retinoic acid tetrabutylammonium salt

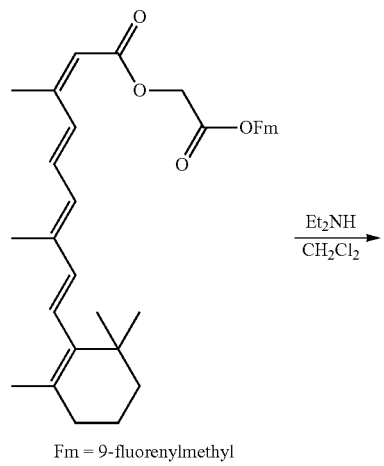

Fm = 9-fluorenylmethyl

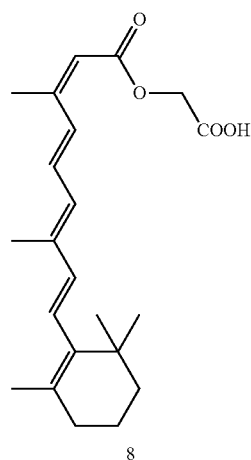

8

The acid 8 was used for preparing a conjugate with CEP-701 (CEP-glycol-Ret), according to Scheme 7.

Scheme 7. Synthesis of CEP-glycol-Ret

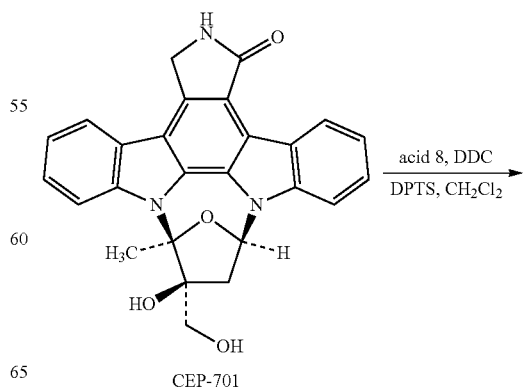

CEP-701

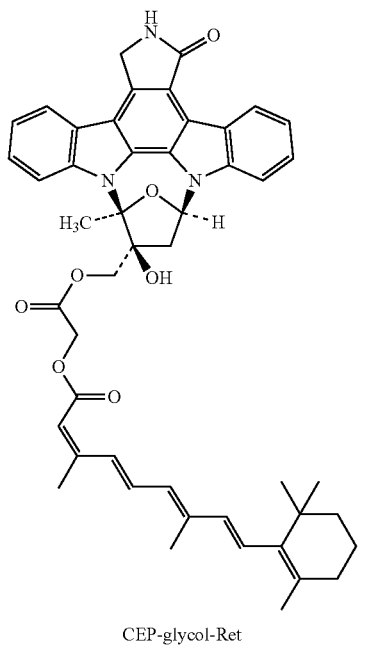

CEP-glycol-Ret

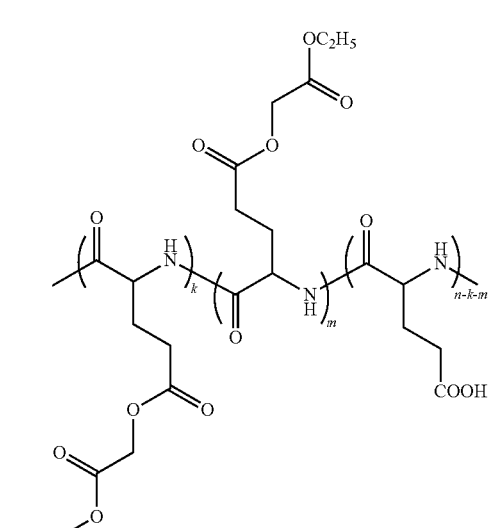

2'-PTX n = ca. 100; k = 0.45 n; m = 0.40 n

Analogous conjugates with CEP-751, PTX or sirolimus may be made with suitable modifications of the above approach.

Another variant of PTX prodrugs according to the invention is provided by attachment of PTX to a biocompatible polymer (e.g., poly-L-glutamic acid) via analogous rapidly hydrolysable ester bridges (e.g., acylglycine or acyloxyacetate esters). One method for preparing such prodrugs is by reaction of PTX 2'-bromoacetate with the tetrabutylammonium salt of poly-L-glutamic acid in 1-methylpyrrolidinone (1-MP) solutions, resulting in the formation of rapidly cleavable acyloxyacetate ester bridges between the polymer and PTX (Scheme 8).

Scheme 8.
Synthesis of polymer-bound PTX
prodrug based on poly-L-glutamic acid

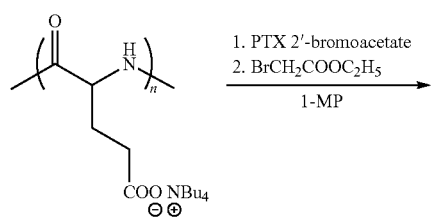

Poly-L-glutamic acid
tetrabutylammonium salt

Due to steric hindrance, it is difficult to attach PTX to more than about half of the glutamic acid units. Thus, in some embodiments most of the unreacted carboxylic groups are transformed into non-charged functionalities (e.g., by esterification, such as an ethyl or methyl ester). When a polyglutamate-bound PTX prodrug formed at this or similar molar modification ratio and having a molecular weight exceeding 2 kDa is used, the release of PTX is expected to be dominated by the kinetics of the ester bridge hydrolysis. Polymer-bound PTX prodrugs based on poly-L-glutamic acid eventually form L-glutamic acid, a natural metabolic material, as a degradation by-product. Other suitable biocompatible polymers include poly-γ-glutamic acid, poly-L-aspartic acid and hyaluronic acid. Reaction of PTX 2'-bromoacetate with tetrabutylammonium salts of non-polymeric carboxylic acids can also be used as a way of preparing other easily cleavable PTX prodrugs, not necessarily polymer-bound. Suitable non-polymeric carboxylic acids include fatty acids. Specific useful acids include palmitic, stearic, oleic, ricinoleic, docosahexaenoic and retinoic acids.

Rapidly Cleavable Prod Rugs Incorporating 2-Ketocarboxylic Acids as a Hydrolyzable Linker For some pro-drugs (e.g., CEP-701 conjugates), a further increase in the rate of hydrolytic cleavage is sometimes desirable in order to provide therapeutically adequate levels of the pharmacologically active compound. It has now been found that this can be achieved by using a new linking ester bridge derived from 2-ketocarboxylic acids. Conjugates with 2-ketocarboxylic ester linkages are found in compounds according to formula (I) in which m=0. Due to the influence of the adjacent carbonyl, the carboxylic group of 2-keto-acids is approximately an order of magnitude more acidic compared with that of O-acylated glycolic acid derivatives. Therefore, a much more rapid cleavage is possible for pro-drugs based on the esters of 2-keto-acids. 2-Ketoglutaric acid is an example of a non-toxic, biodegradable 2-keto-acid readily eliminated in the body via the citric acid cycle. Due to its biocompatibility and bioeliminability it was chosen here as a candidate for demonstrating the feasibility of this novel strategy and for constructing cleavable drug conjugates, where the most acidic 1-COOH of 2-ketoglutaric acid was used for forming a rapidly cleavable ester bond with the OH-group of the drug, whereas the 5-COOH was applied as a tether for a lipophilic residue (e.g., α-tocopheryl). 4-(α-Tocopheryloxycarbonyl)-2-ketobutyric acid (7) was synthesized according to Scheme 9, as a representative example of a lipophilic and biocompatible 2-keto-acid suitable for preparing rapidly cleavable drug conjugates. The synthesis included preparation of the 1-mono-(p-methoxybenzyl) ester of 2-ketoglutaric acid (3), which exists in solutions as an equilibrium mixture of tautomers (3a and 3b), protection of the keto-group with formation of the silylated enol (4), esterification of the 5-COOH with α-tocopherol and subsequent removal of the protective groups. Acid 7 was then coupled with PTX to produce the rapidly cleavable PTX-conjugate (2'-PTX-ketoglut-Toc), according to Scheme 10. Due to an increased lability of this PTX conjugate, the procedure was modified with respect to that used for the synthesis of 2'-PTX-glycol-suc-Toc, and was carried out using a lower reaction temperature and deactivated silica-gel during the purification step.

Scheme 9. Synthesis of 4-(α-tocopheryloxycarbonyl)-2-ketobutyric acid 7

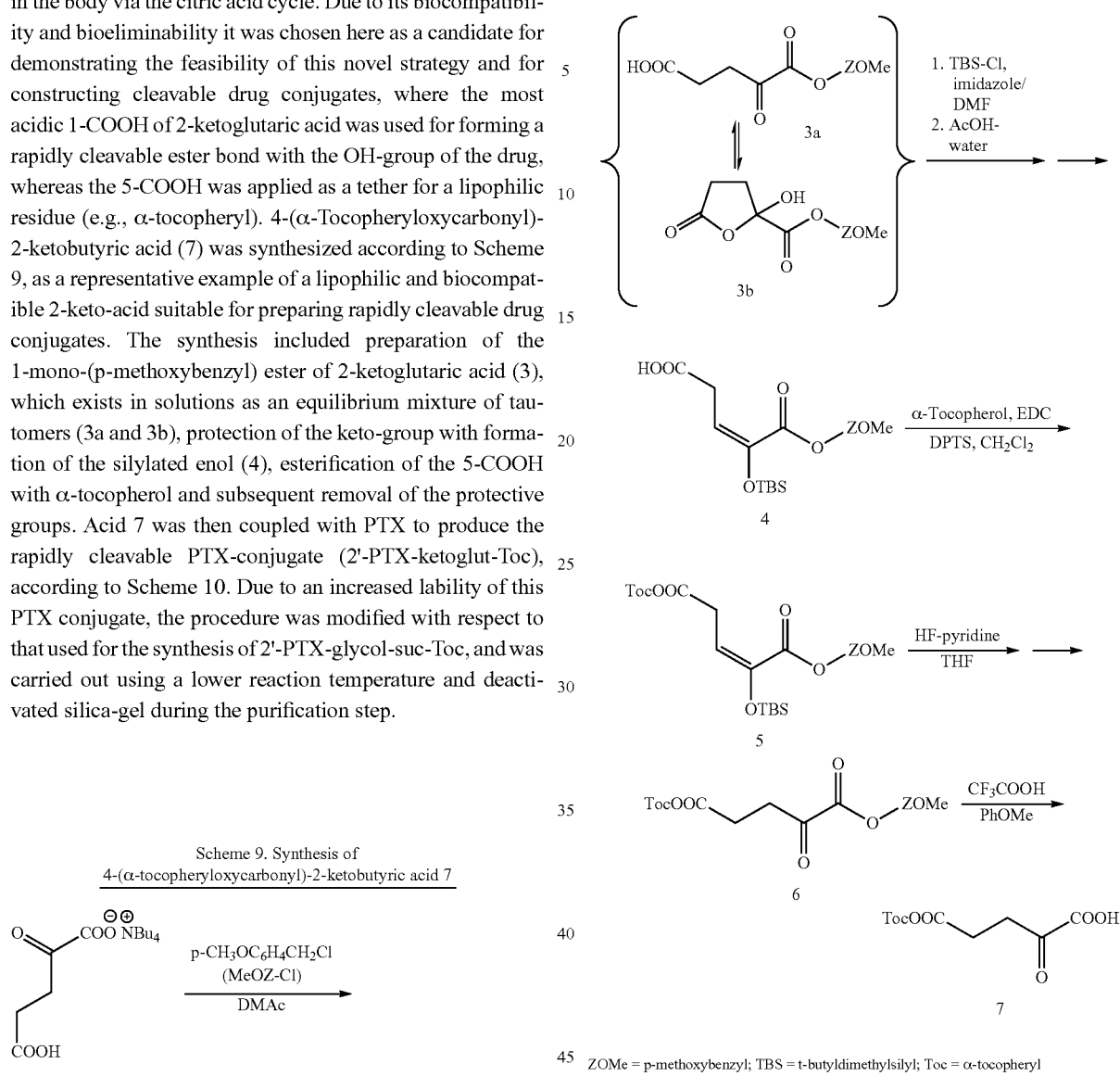

ZOMe = p-methoxybenzyl; TBS = t-butyldimethylsilyl; Toc = α-tocopheryl

Scheme 10. Synthesis of the conjugate 2'-PTX-ketoglut-Toc

Analogous conjugates with CEP-751, CEP-701 or sirolimus may be made with suitable modifications of the above approach.

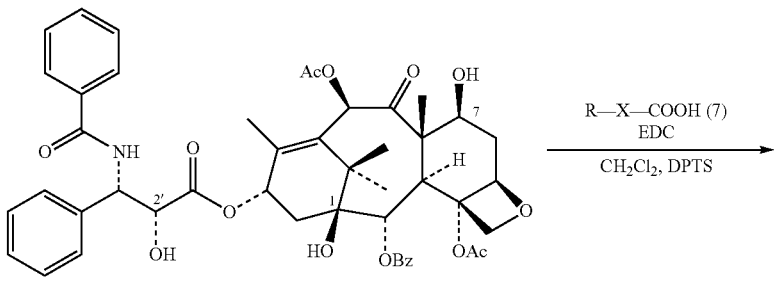

-continued

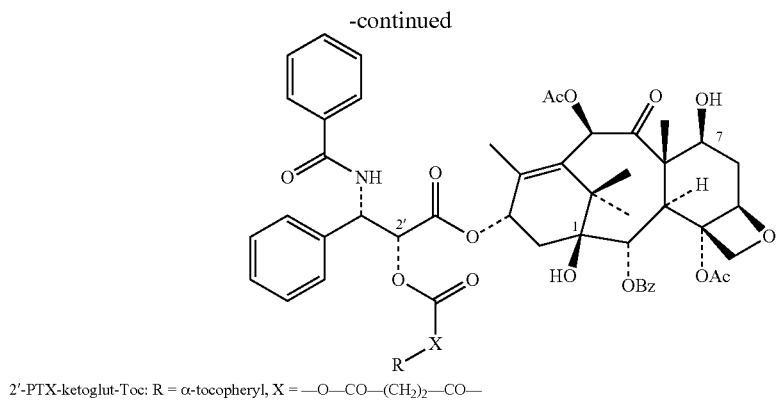

2'-PTX-ketoglut-Toc: R = α-tocopheryl, X = —O—CO—(CH$_2$)$_2$—CO—

Preparation and Targeting of MNP Containing Rapidly Cleavable Prodrugs

MNP containing prodrugs according to the invention may be prepared using methods described in US 2009-0216320 A1 and US 2009-0082611 A1, or minor modifications of these methods. In addition to the prodrug, the MNP each contain one or more individual magnetic or magnetizable nanocrystal(s) and one or more water-insoluble biocompatible materials to bind the MNP together. The nanocrystals may include ones that are permanently magnetic and/or ones that are magnetizable upon exposure to an external magnetic field, but lose their magnetization when the field is removed. Superparamagnetic materials are examples of materials that lose their magnetic moments when the field is removed, and in some embodiments the MNP include superparamagnetic materials to prevent irreversible aggregation of the particles. Examples of suitable superparamagnetic materials include, but are not limited to, mixed iron oxide (magnetite), or gamma ferric oxide (maghemite) as well as substituted magnetites that include additional elements such as zinc or manganese. Preferably, the superparamagnetic material is in the form of one or more nanocrystals, for example, single-domain crystalline systems with at least one dimension ≤100 nm. Although it retains some magnetization after a magnetic field is removed, elemental iron may also be used in some embodiments as it exhibits a significantly stronger magnetization than magnetite. As used herein, the term "nanocrystal" means any particle with at least one dimension ≤100 nm and that is single crystalline or monocrystalline, formed of a single crystal unit, such that all elements have identical crystallographic orientation of c- and a-axes and overgrow as one unit.

The biocompatible material may be a polymer and may be either biodegradable or non-biodegradable. Non-limiting examples of suitable polymers include poly(urethane), poly (ester), poly(lactic acid), poly(glycolic acid), poly(lactide-co-glycolide), poly(ε-caprolactone), poly(ethyleneimine), polystyrene, polyamide, rubber, silicone rubber, poly(acrylonitrile), polyacrylate, poly(methacrylate), poly(α-hydroxy acid), poly(dioxanone), poly(orthoester), poly(ether-ester), poly(lactone), poly(alkylcyanoacrylate), poly(anhydride), poly(ethylene vinyl acetate), poly(hydroxybutyrate), poly (tetrafluoroethylene), poly(ethylene terephthalate, polyoxyethylene, polyoxyethylene-polyoxypropylene block copolymers, mixtures thereof and copolymers of corresponding monomers.

In an exemplary embodiment, MNP can be prepared by dispersing the nanocrystals in an organic solvent, in which the biocompatible material and/or the prodrug is dissolved, emulsifying the organic phase in water in the presence of a suitable stabilizer, and finally eliminating the solvent to obtain solidified MNP. The temperature for nanoparticle preparation is typically in a range from about 25° C. to about 37° C., although higher or lower temperatures can be used. Non-limiting examples of ways to prepare superparamagnetic nanoparticles for biological applications are described in U.S. Pat. Nos. 7,175,912 and 7,175,909, and U.S. Publ. No. 20050271745.

The magnetic nanoparticles carrying the prodrug typically range in size from about 50 to about 500 nm. The size may vary according to any appropriate variable. More typically the nanoparticles range in size from about 50 nm to about 400 nm, and most typically from about 100 nm to about 350 nm.

The nanoparticle may be derivatized, and the surface of the particle can be modified to facilitate derivatization. For example, the particles can be coated with a thiol-reactive and photoactivatable polymer. Irradiation can facilitate the covalent binding of the polymer to the surface, and its thiol-reactive groups can subsequently be used to attach agents providing stealth properties in the blood circulation and/or specific binding to a target tissue. Photochemical activation of surfaces for attaching biomaterials is described in U.S. Pat. No. 7,635,734.

Magnetically responsive nanoparticles containing prodrugs according to the invention may be delivered to a patient and targeted to a desired site using one or more magnets to direct the particles. Such methods are described in US 2009-0216320 A1 and US 2009-0082611 A1. In particular, the uniform field-controlled targeting approach discussed in the latter published application may be advantageously applied to MNP according to the invention. Application to both coronary and peripheral arteries is possible, as is application to veins. In some aspects the invention provides a system comprising MNP, a stent (for example made of 304 grade or other stainless steel) and a source of a magnetic field. The field produces temporary magnetization of the stent and/or the MNP and thereby allows targeted delivery of the MNP to the stent. In some embodiments the magnetic field is relatively uniform. For example, the field may be sufficiently uniform such that the applied field strength varies by at most 1% across the shortest dimension (i.e., the diameter) of the stent. A uniform magnetic field may advantageously be produced by a combination of two or more magnets, any/all of which may be either permanent or electromagnets. A strong, far-reaching field may thus be applied to magnetize the particles and induce high magnetic field gradients at the site of the stent, resulting in increased particle accumulation and retention in the stented region. In some embodiments, the target (such as a stent) is situated between two opposed magnets.

EXAMPLES

Example 1

Preparation of N-(3-cholesteryloxycarbonyl)propionylglycine (1)

A method according to Scheme 2 was followed. Cholesteryl hemisuccinate (1.019 g, 2.09 mmol), N-hydroxysuccinimide (SuOH, 0.300 g, 2.55 mmol) and 1-ethyl-3-(3-dimethylaminopropyl)carbodiimide hydrochloride (EDC, 0.550 g, 2.86 mmol) were stirred in $CH_2Cl_2$ (15 mL) at room temperature for 16 h. The solvent was removed, the residue was suspended in 10% aqueous $NaH_2PO_4$ (12 mL, acidified with $H_3PO_4$ to pH=3), the precipitate was filtered off, washed with water, dissolved in $CHCl_3$ and dried over $Na_2SO_4$. The solution was filtered through silica-gel and dried. The residual solid (1.172 g) was dissolved in $CH_2Cl_2$ (6 mL) and added dropwise in 5 min. To a solution of tetrabutylammonium glycinate (5 mmol, prepared from equimolar amounts of glycine and aqueous 40% tetrabutylammonium hydroxide and dried by co-evaporations with 2-propanol) in $CH_2Cl_2$ (10 mL) at 0° C. The mixture was further stirred at 0° C. for 1 h, dried in vacuo, diluted with aqueous 0.5 M $NaHSO_4$ (50 mL) and extracted with ethyl acetate (80 mL). The organic phase was washed with 0.5 M $NaHSO_4$ and with water, the solvent was removed, the residue was purified by flash-chromatography on silica-gel in $CHCl_3$-2-propanol (100:0 to 10:1) and recrystallized from cold (−20° C.) $CHCl_3$. Yield of 1: 0.814 g (71%), the structure and purity were confirmed by $^1$H NMR.

Example 2

Preparation of Acids 2a and 2b

A method according to Scheme 3 was followed. β-Cholesteryl hemisuccinate (1.000 g, 2.05 mmol) was neutralized with an equimolar amount of aqueous 40% tetrabutylammonium hydroxide. The resulting $Bu_4N$-salt was dried by co-evaporations in vacuo with 2-propanol and heptane, dissolved in 1-methylpyrrolidinone (7 mL), cooled to 0° C. and protected with the argon atmosphere. tert-Butyl bromoacetate (0.38 mL, 2.5 mmol) was added, the mixture was stirred at 0° C. for 1 h and diluted with water (20 mL). The precipitate was filtered off, washed with water, dissolved in $CH_2Cl_2$ and purified on silica-gel. The resulting tert-butyl ester of 2a (ca. 1.1 g) was dissolved in dry $CH_2Cl_2$ (3.5 mL), protected with argon, and trifluoroacetic acid (2.2 mL) followed by triethylsilane (1.1 mL) were added. The mixture was left at 23° C. for 1.2 h, and dried in vacuo. The residue was washed with water and crystallized from pentane. Yield of 2a: 0.968 g (86%).

Analogously, 2b was prepared from D-α-tocopheryl hemisuccinate in an 84% yield. Instead of crystallization, flash chromatography on silica-gel ($CHCl_3$-MeCN, 100:0 to 6:1) was used for the purification of 2b. The structures and purity of acids 2a,b were confirmed by $^1$H NMR and TLC ($SiO_2$, $CHCl_3$-MeCN-AcOH, 80:20:1).

Example 3

Preparation of PTX 2'-Esters

A method according to Scheme 4 was followed. PTX (100 mg, 0.117 mmol) and the corresponding acid (0.124 mmol) were dissolved in $CH_2Cl_2$ (2 mL). DPTS catalyst (80 mg, 0.27 mmol) and EDC (48 mg, 0.25 mmol) were added, the mixture was stirred at 23° C. for 2 h and dried in vacuo. Aqueous 10% solution of $NaH_2PO_4$ (30 mL, acidified with $H_3PO_4$ to pH=3) was added, the mixture was extracted with ethyl acetate (30 mL), the organic phase was washed with the solution as above, freed from droplets of aqueous phase and dried. The residue was purified by flash chromatography on silica-gel using mixtures of ethyl acetate and hexane. For 2'-PTX-glycine-suc-Chol an additional chromatography in a different solvent system ($CHCl_3$-MeOH) was required. The yields are given below in Table 1. The structures and purity of compounds were verified by $^1$H NMR and TLC ($SiO_2$, ethyl acetate-heptane, 3:2 and $CHCl_3$-MeOH, 95:5 for 2'-PTX-glycine-suc-Chol).

TABLE 1

Synthesis of PTX 2'-esters.

| PTX conjugate | Yield |
|---|---|
| 2'-PTX-glycine-suc-Chol | 41% |
| 2'-PTX-glycol-suc-Chol | 81% |
| 2'-PTX-glycine-suc-Toc | 84% |
| 2'-PTX-suc-chol | 82% |

Example 4

Preparation of PTX 2'-bromoacetate

Bromoacetic acid (35.5 mg, 0.253 mmol) and PTX (205 mg, 0.24 mmol) were dissolved at 0° C. in dichloromethane (6 mL). DPTS catalyst (60 mg, 0.20 mmol) and 1,3-dicyclohexylcarbodiimide (DCC, 87 mg, 0.42 mmol) were added, the mixture was stirred at 0° C. for 1 h, and the precipitate of dicyclohexylurea was filtered off from the cold mixture. The filtrate was diluted with cold ethyl acetate (35 mL), washed with aqueous 0.1 M solution of citric acid, with water, freed of water droplets, and the solvents were distilled off in vacuo. The residue was extracted with cold pentane to remove the excess of DCC, dissolved in ethyl acetate (2.5 mL) filtered and purified by flash chromatography on silica-gel, eluting with hexane-ethyl acetate (2:1 to 1:1). Yield of PTX 2'-bromoacetate: 212 mg (91%), the structure and purity were confirmed by $^1$H NMR and TLC ($SiO_2$, ethyl acetate-heptane, 3:2).

Example 5

Preparation of Polymer-Bound PTX Prodrug Based on poly-L-glutamic Acid

A method according to Scheme 8 was followed, using PTX 2'-bromoacetate as prepared in Example 4. Sodium salt of poly-L-glutamic acid (Alamanda Polymers, Huntsville, Ala., $M_n$≈15 kDa, n≈100) was treated with Dowex-50 (acid-form) in an aqueous solution, the free polymeric acid was neutralized with tetrabutylammonium hydroxide to pH=7, and the resulting tetrabutylammonium salt was dried by co-evaporations with 2-propanol, $CHCl_3$ and heptane. The dry polymer (82 mg, containing 0.175 mmol of $Bu_4N^+$) was dissolved in dry 1-MP (0.6 mL) at 0° C. under argon protection. PTX 2'-bromoacetate (100 mg, 0.102 mmol) was added, the mixture was stirred at 0° C. for 0.5 h, and ethyl bromoacetate (0.1 mL, 0.9 mmol) was introduced. After another 1.5 h at 0° C., the mixture was diluted with aqueous 0.1 M solution of citric acid (25 mL), the precipitate was filtered off, washed with 0.1 M citric acid, with water, and dissolved in $CHCl_3$ (5 mL). The polymer was purified from non-polymeric impurities by several precipitations from $CHCl_3$-solutions with equal volumes of heptane and dried in vacuo. Yield: 115 mg. $^1H$ NMR analysis found 45% of the polymer links bearing the PTX residues, whereas 40% of the carboxylic functions were modified with ethoxycarbonylmethyl groups. The rest (15%) of links remained non-modified. TLC ($SiO_2$, ethyl acetate-heptane, 3:2) showed no mobile non-polymeric impurities.

Example 6

Preparation of CEP-glycol-suc-Chol

A method according to Scheme 5 was followed. CEP-701 (Cephalon, Frazer, Pa., 83 mg, 0.188 mmol), acid 2a (110 mg, 0.202 mmol), DPTS catalyst (125 mg, 0.42 mmol) and EDC (79 mg, 0.41 mmol) were combined in dichloromethane (3 mL) and stirred at 23° C. for 3 h. Aqueous 10% solution of $NaH_2PO_4$ (50 mL, acidified with $H_3PO_4$ to pH=3) was added, the mixture was extracted with ethyl acetate (40 mL), the organic phase was washed with water, dried over $Na_2SO_4$, and the solvent was evaporated in vacuo. The residue was purified by flash chromatography on silica-gel using mixtures of chloroform and ethyl acetate (100:0 to 2:1). Yield of CEP-glycol-suc-Chol: 147 mg (81%), the structure and purity were confirmed by $^1H$ NMR and TLC ($SiO_2$, ethyl acetate-$CHCl_3$, 1:1).

Example 7

Formulation of MNP with PTX and PTX Prodrugs

Polylactide-based MNP were formulated with inclusion of nanocrystalline magnetite by a modification of the emulsification-solvent evaporation method. Ferric chloride hexahydrate and ferrous chloride tetrahydrate (170 and 62.5 mg, respectively) were dissolved in ethanol (2.5 mL) and mixed with freshly prepared aqueous sodium hydroxide (0.5 N, 5 mL). The precipitate was heated for 1 min at 90° C., cooled on ice, and separated on a magnet. The obtained magnetite was stirred with a solution of oleic acid in ethanol (150 mg in 2 mL) at 90° C. for 5 min. Free oleic acid was separated by deionized water. Magnetite was washed with ethanol, dispersed in 8 mL of chloroform, and used to dissolve 100 mg of poly(D,L-lactide) (molecular weight 75,000-120,000 Da) and 15 mg PTX or a PTX prodrug. The organic dispersion was emulsified by sonication on ice in 10 mL of an aqueous solution of bovine serum albumin (1% w/v), and the organic solvent was evaporated under reduced pressure. MNP were washed twice by magnetic decantation, resuspended in 6 mL of aqueous trehalose (10% w/v), passed through a sterile 5 μm filter unit and lyophilized. Lyophilized MNP were kept at −80° C. and resuspended in deionized water before use.

In Vitro Testing

Example 8

A10 Growth Inhibition by Rapidly Cleavable Hydrophobic PTX Derivatives Vs. Controls A therapeutically relevant growth inhibitory effect of the rapidly activatable hydrophobic PTX derivatives was demonstrated using cultured rat aortic smooth muscle cells (A10) in comparison with PTX and a control hydrophobic derivative formed using a regular ester linkage. PTX and its hydrophobic derivatives were dissolved in dimethyl sulfoxide and further diluted in cell culture medium, so that the final concentration of dimethyl sulfoxide did not exceed 0.1%. Cells seeded at 10% confluency on 96-well plates were incubated with the compounds at indicated PTX molar equivalent doses for 2 hr, and the cell viability was compared to that of untreated cells 7 days post treatment using the Alamar Blue assay. The results are shown in FIG. 1.

While the rapidly activatable PTX prodrugs 2'-PTX-glycine-suc-Chol and 2'-PTX-glycol-suc-Chol mediated a dose-dependent A10 cell growth inhibition, no growth inhibition was observed with the PTX conjugate employing a standard ester linkage not according to the invention, confirming the importance of the rapidly cleavable linker between PTX and cholesterol for the biological effect.

Example 9

Figure 2:
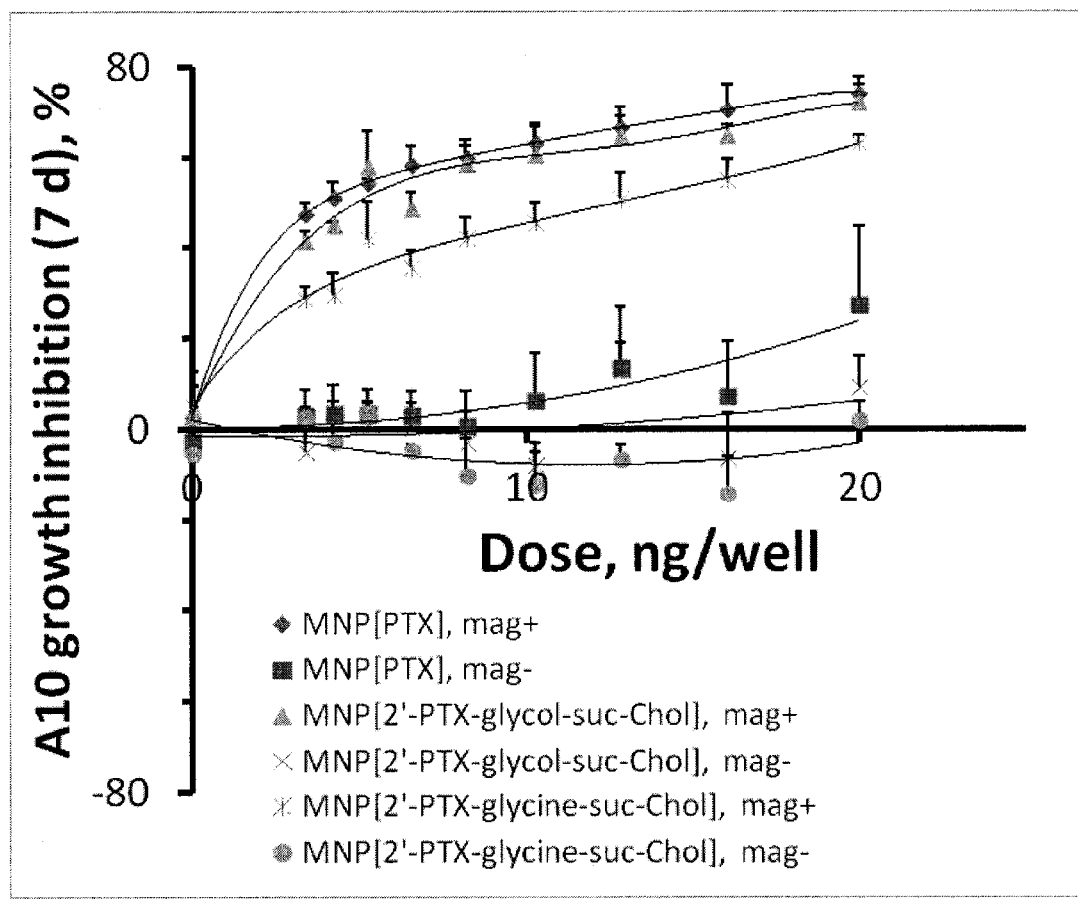
FIG. 2 shows the results of a study of A10 growth inhibition by magnetically guided MNP loaded with rapidly cleavable hydrophobic PTX derivatives according to the invention, vs. MNP containing PTX.

A10 Growth Inhibition by Magnetically Guided MNP Loaded with Rapidly Cleavable Hydrophobic PTX Derivatives Vs. PTX Magnetically guided A10 growth inhibition mediated by MNP loaded with the rapidly cleavable PTX derivatives was demonstrated in comparison with PTX-loaded MNP and respective non-magnetic controls. Cells were incubated with indicated doses of the compounds formulated in MNP for 5 min with or without (mag+ or mag−) the presence of a high gradient magnetic field (average field gradient of 32.5 T/m). Cell viability was determined as above 7 days post treatment. The results are shown in FIG. 2.

Significant cell growth inhibition was observed following the brief exposure to the magnetic field with MNP-encapsulated rapidly cleavable PTX derivatives. For both 2'-PTX-glycol-suc-Chol and 2'-PTX-glycine-suc-Chol, activity was comparable to that of MNP loaded with PTX. In contrast to PTX-loaded MNP, no growth inhibition was observed with MNP-encapsulated prodrugs under the non-magnetic control treatment conditions, suggesting that these formulations are less prone to causing non-specific toxicity resulting from prematurely released drug. In sum, the activity of freshly applied MNP loaded with PTX prodrugs according to the invention was roughly equivalent to that of PTX MNP.

Example 10

Figure 3:
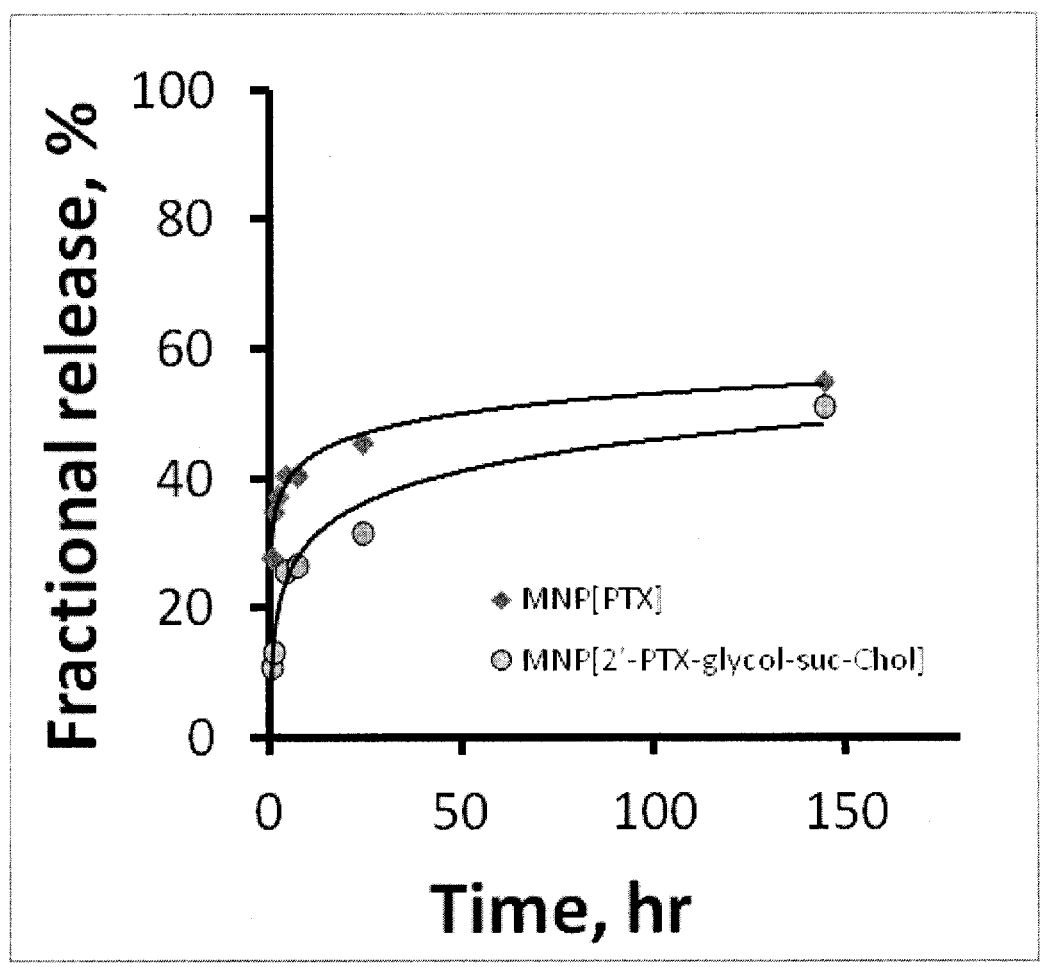
FIG. 3 shows in vitro release kinetics from MNP and recovery of 2'-PTX-glycol-suc-Chol, vs. PTX.

In Vitro Release Kinetics and Recovery of 2'-PTX-glycol-suc-Chol Vs. PTX from MNP The release of 2'-PTX-glycol-suc-Chol from MNP was measured in comparison with PTX using the external sink method. A 1:1 mixture of heptane and 1-octanol was used as the acceptor medium to ensure perfect sink conditions. MNP were diluted 1:500 in phosphate buffer containing 2% bovine serum albumin, included to more closely model in vivo conditions. Released drug was assayed spectrophotometrically in the acceptor phase at predetermined timepoints (λ=230 nm). After five days the amount of the compounds remaining in MNP was measured following extraction in 1-octanol. The results are shown in FIG. 3.

A total of 81% of 2'-PTX-glycol-suc-Chol was recovered in the release medium samples and upon the experiment termination, with 30% of the initial drug payload still present in the MNP. In contrast, a total of only 55% of the PTX was recovered, and none of it was still retained in the MNP at the end of the 5-day experiment. Thus, 2'-PTX-glycol-suc-Chol exhibited significantly slower release kinetics and was better protected from degradation than PTX. These results suggest that under in vivo conditions, 2'-PTX-glycol-suc-Chol may be expected to provide therapeutically adequate local drug concentrations at the site of arterial injury over an extended period of time, and significantly longer than that provided by PTX itself. This expectation is further supported by the results of Example 11.

Example 11

A10 Inhibition by 2'-PTX-glycol-suc-Chol Vs. PTX Following 4-Day incubation with Fetal Bovine Serum at 37° C.

Figure 4:
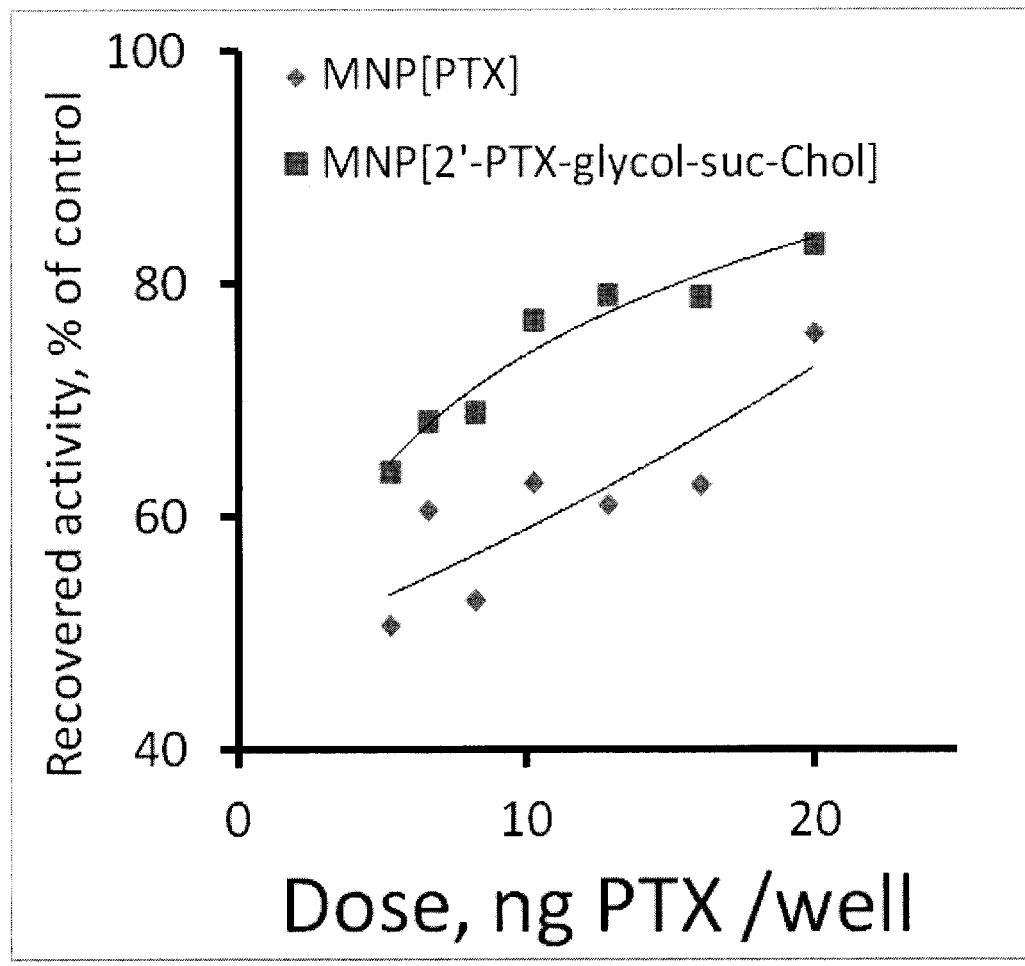
FIG. 4 shows A10 inhibition by 2'-PTX-glycol-suc-Chol vs. PTX following 4-day incubation with FBS at 37° C.

MNP loaded with 2'-PTX-glycol-suc-Chol or PTX at 1 mg/mL were diluted 1:500 in fetal bovine serum (FBS), placed on a tube rotator and incubated for 4 days at 37° C. modeling the exposure of stent-targeted MNP to the in vivo environment. MNP suspensions were then applied to A10 cells for 5 min in the presence of a high gradient magnetic field (See Example 9) in a dose range equivalent to 5-20 ng drug per well based on their initial drug loading. Their growth inhibitory effect was compared with that of fresh MNP applied in equivalent dilutions under magnetic conditions, and the ratio between their respective inhibition efficiencies was plotted as Recovered activity, % of control (See FIG. 4). In agreement with its slower release kinetics resulting in a better protection and minimized hydrolytic inactivation, 2'-PTX-glycol-suc-Chol formulated in MNP retained a larger fraction of its initial activity compared to PTX following the exposure to model in vivo conditions.

Example 12

Preparation of 4-(α-tocopheryloxycarbonyl)-2-ketobutyric acid (7)

a). 2-Ketoglutaric acid 1-(p-methoxybenzyl) ester (3)

2-Ketoglutaric acid (98.5%, 1.484 g, 10.0 mmol) was suspended in 2-propanol (25 mL), cooled in ice and neutralized with a 40% aqueous solution of tetrabutylammonium hydroxide (5.9 mL, 9.0 mmol). The resulting solution was diluted with hexane (7 mL), dried in vacuo (below 30° C.), dissolved in a mixture of 2-propanol (15 mL) and hexane (5 mL) and dried as above to a viscous syrup (4.834 g). The residue was protected with argon, dissolved in N,N-dimethylacetamide (5 mL), and p-methoxybenzyl chloride (1.25 mL, 9.0 mmol) was added. The mixture was allowed to react at room temperature under argon protection for 65 h. An 0.8 M aqueous solution of phosphoric acid (40 mL) was added, the mixture was extracted with ethyl acetate, the organic layer was washed with 0.8 M phosphoric acid, with water, and dried. The crude monoester (2.266 g) was purified by flash chromatography (silica-gel, chloroform-ethyl acetate, 100:0 to 1:1, containing 0.2% of acetic acid) and crystallized from ethyl acetate-hexane. Yield of 3: 1.330 g (56%), $^1$H NMR (CDCl$_3$) detected 60% of the open tautomer 3a and 40% of the cyclic tautomer 3b.

b). Compound 4 tert-Butyldimethylsilyl chloride (97%, 0.515 g, 3.31 mmol) and imidazole (99%, 0.467 g, 6.79 mmol) were mixed in DMF (0.90 mL), and the monoester 3 (0.239 g, 0.90 mmol) was added. The mixture was stirred at room temperature for 2.5 h under argon protection, diluted with 0.5 M aqueous phosphoric acid (30 mL) and extracted with ethyl acetate (30 mL). The organic layer was washed with 0.5 M phosphoric acid and with water, dried in vacuo (up to 0.1 mm Hg, below 30° C.), and the residue (0.482 g) was stirred with a mixture of acetic acid (6 mL) and water (3 mL) at room temperature for 0.5 h. Volatiles were removed in vacuo as above, the crude 4 was purified by flash chromatography (silica-gel, chloroform-ethyl acetate, 100:0 to 10:1), solidified by co-evaporation with pentane and evacuated at 0.1 mm Hg. Yield of 4: 0.288 g (84%). $^1$H NMR (CDCl$_3$), δ, ppm: 0.12 (s, 6H), 0.91 (s, 9H), 3.26 (d, 7 Hz, 2H), 3.79 (s, 3H), 5.11 (s, 2H), 6.12 (t, 7 Hz, 1H), 6.87 (d, 9 Hz, 2H), 7.29 (d, 9 Hz, 2H).

c). Compound 5

The protected acid 4 (94 mg, 0.25 mmol) was reacted in dichloromethane (2.6 mL) with α-tocopherol (95%, 141 mg, 0.31 mmol) and EDC (98 mg, 0.50 mmol) in the presence of DPTS (110 mg, 0.37 mmol) at room temperature for 2 h. Aqueous 10° 70 solution of NaH$_2$PO$_4$ (20 mL, acidified with H$_3$PO$_4$ to pH=3) and water (20 mL) were added, the mixture was extracted with ethyl acetate (25 mL), the organic phase was washed with water and dried. The residue was purified by flash chromatography (silica-gel, hexane-ethyl acetate, 100:0 to 10:1). According to $^1$H NMR, the purified compound 5 (178 mg, 64%) still contained 30% of α-tocopherol, which was possible to separate only at the next step.

d). Compound 6

Under ice-cooling, HF-pyridine complex (70:30, 0.30 mL, containing 12.0 mmol of HF and 1.3 mmol of pyridine) was diluted with THF (1.0 mL) and neutralized with pyridine (0.94 mL, 11.6 mmol). The compound 5 (176 mg, containing 123 mg, 0.155 mmol of the pure compound) was dissolved in the resulting mixture and allowed to react for 2 h at room temperature under argon protection. After cooling to 0° C., ice-cold water (10 mL) and KHCO$_3$ (1.29 g, 12.9 mmol) were added. The mixture was extracted with ethyl acetate, the organic layer was washed with 0.5 M aqueous citric acid, with water and dried. The crude 6 (166 mg) was purified by flash chromatography (silica-gel, hexane-ethyl acetate, 100:0 to 7:1). Yield of 6: 87 mg (83%). The structure and purity were confirmed by TLC and $^1$H NMR.

e). Compound 7

The ester 6 (86 mg, 0.126 mmol) was dissolved in anisole (0.7 mL), and CF$_3$COOH (0.35 mL) was added. The mixture was left at room temperature for 0.5 h and evacuated (vacuum to 0.1 mm Hg) at room temperature. The residue (98 mg) was purified by flash chromatography (silica-gel, CHCl$_3$-MeCN, 30:1 to 5:1). Yield of 7: 42 mg (59%). The structure and purity were confirmed by TLC and $^1$H NMR.

Example 13

Preparation of cleavable PTX 2' ester 2'-PTX-ketoglut-Toc

The acid 7 (42 mg, 0.075 mmol) and PTX (64 mg, 0.075 mmol) were combined at 0° C. in dichloromethane (2 mL). DPTS catalyst (20 mg, 0.068 mmol) and EDC, (29 mg, 0.15 mmol) were added, the mixture was stirred at 0° C. for 1 h and diluted with a cold 5% aqueous solution of NaH$_2$PO$_4$ (30 mL, acidified with H$_3$PO$_4$ to pH=3). The product was extracted with ethyl acetate and purified by flash chromatography (silica-gel deactivated with $CF_3COOH$, hexane-ethyl acetate, 4:1 to 1:1). Yield of 2'-PTX-ketoglut-Toc: 66 mg (62%). The structure and purity were confirmed by TLC and $^1H$ NMR.

Example 14

Preparation of 13-cis-retinoyloxyacetic acid (8)

a). 9-Fluorenylmethyl bromoacetate

Under ice-cooling, 9-fluorenemethanol (99%, 0.694 g, 3.5 mmol), bromoacetic acid (99%, 0.406 g, 2.9 mmol), DPTS (0.130 g, 0.44 mmol) and DCC (99%, 0.729 g, 3.5 mmol) were combined in dichloromethane (9 mL), stirred at 0° C. for 1 h, and the precipitate of dicyclohexylurea was filtered off from the cold mixture. The filtrate was diluted with cold ethyl acetate (30 mL), washed twice with cold 5% aqueous solution of $NaH_2PO_4$ (60 mL, acidified with $H_3PO_4$ to pH=3), freed of water droplets, and the solvents were distilled off in vacuo. The residue was extracted with cold pentane to remove the excess of DCC, and purified by flash chromatography (silica-gel, hexane-$CHCl_3$, 5:1 to 1:1) followed by crystallization from cold hexane. Yield of 8: 0.795 g (87%). The purity was confirmed by TLC ($SiO_2$, heptane-ethyl acetate, 9:1).

b). 13-cis-Retinoyloxyacetic acid 8

13-cis-Retinoic acid (98%, 250 mg, 0.815 mmol) was added to a $CO_2$-saturated mixture of 40% aqueous tetrabutylammonium hydroxide solution (547 mg, 0.843 mmol) and 2-propanol (5 mL). After a complete homogenization, the mixture was diluted with heptane (2 mL) and dried in vacuo up to 1 mm Hg at 25° C. The residue (586 mg) was dissolved in dry 1-MP (2.5 mL) at 0° C., and 9-fluorenylmethyl bromoacetate (284 mg, 0.89 mmol) was added. The mixture was stirred under argon protection for 2 h at 0° C., diluted with water (70 mL) and extracted with ethyl acetate (40 mL). The organic layer was washed with water and dried, the residue (0.529 g) was purified by flash chromatography (silica-gel, hexane-$CHCl_3$, 3:2 to 0:100), the ester (420 mg) was dissolved in $CH_2Cl_2$ (3.1 mL), and diethylamine (3.1 mL) was added. The mixture was allowed to react at room temperature for 3 h under argon protection. The solvents were removed in vacuo, the residue was acidified with 1 M aqueous $NaHSO_4$ (20 mL) and extracted with ethyl acetate (25 mL). The organic layer was washed with 0.1 M citric acid, dried, and the residue (0.404 g) was purified by flash chromatography (silica-gel, $CHCl_3$-MeCN, 100:0 to 15:1) followed by crystallization from cold pentane. Yield of 8: 212 mg (72%). The structure and purity were confirmed by TLC and $^1H$ NMR.

Example 15

Preparation of cleavable CEP-701 conjugate CEP-glycol-Ret

Under argon protection and ice cooling, CEP-701 (100 mg, 0.227 mmol), acid 8 (85 mg, 0.237 mmol), DPTS catalyst (145 mg, 0.49 mmol) and DCC (99%, 79 mg, 0.41 mmol) were combined in dichloromethane (3.5 mL) and stirred for 3 h at 0° C. then 50 min at room temperature. Aqueous 10% solution of $NaH_2PO_4$ (30 mL, acidified with $H_3PO_4$ to pH=3) and water (30 mL) were added, the mixture was extracted with warm ethyl acetate (150 mL), the organic phase was washed with 0.1 M aqueous citric acid, with water, freed of water droplets, and dried in vacuo. The resulting solid residue (285 mg) was washed with a 1:1 mixture of 2-propanol and tert-butanol, with pentane, dissolved in ethyl acetate (75 mL) at 50° C. and concentrated in vacuo to a small volume (weight of residue: 3.43 g). After 1 h at room temperature, the separated solid was filtered off, washed with ethyl acetate followed by pentane and dried in vacuo. Yield of CEP-glycol-Ret: 155 mg (87%). The structure and purity were confirmed by TLC and $^1H$ NMR.

In Vivo Testing

Example 16

Tumor Growth Inhibitory Effect of Polymer-Bound PTX Prodrug Based on poly-L-glutamic acid in the Murine Xenograft Model of Neuroblastoma A PTX prodrug based on poly-L-glutamic acid (PG-PTX) was synthesized according to the method shown in Scheme 8 using PTX 2'-bromoacetate as prepared in Example 4. To prepare a uniform aqueous dispersion, 40 mg of PG-PTX were dissolved in a mixture of 2 mL of freshly distilled tetrahydrofuran and 3 mL ethanol. Two hundred mg of human serum albumin were separately dissolved in 80 mL deionized water with magnetic stirring. Polymer solution was added into the aqueous phase, and the solvents were removed using a rotary evaporator under gradually reduced pressure at 30° C. The formulation was concentrated, filtered through a 5.0 μm PVDF membrane after adding trehalose to 10% w/v and volume adjustment to 4 mL, then aliquoted, frozen and lyophilized.

The formulation vehicle used as a control in the tumor growth inhibition experiment was a solution of 200 mg human serum albumin and 400 mg trehalose in 4 mL DDW, filtered, aliquoted and lyophilized as above.

Figure 5:
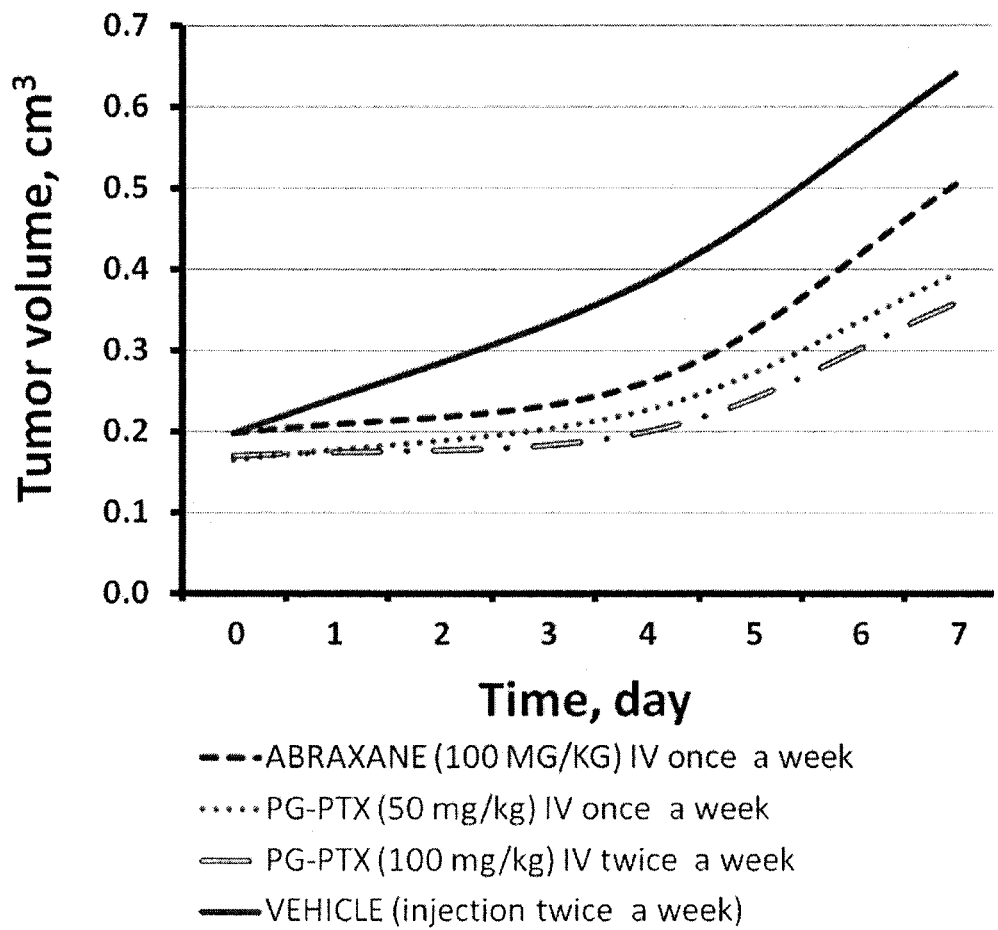
FIG. 5 shows tumor volume as a function of time, using a rapidly cleavable polyglutamate-based paclitaxel prodrug according to the invention in the murine xenograft model of neuroblastoma, compared with the activity of ABRAXANE® treatment.

For the xenograft studies, athymic nu/nu mice (ten animals per group) were injected in the flank with $10^7$ SY5Y-TrkB cells in 0.3 mL MATRIGEL™ matrix (BD Biosciences, Franklin Lakes, N.J.). Treatment was started when the average SY5Y-TrkB tumor size was 0.2 $cm^3$. PG-PTX was administered intravenously through the tail vein either once or twice a week at 50 mg/kg per injection in comparison to the vehicle or a clinically used injectable paclitaxel formulation (ABRAXANE® treatment, 100 mg/kg, once a week, Celgene, Summit, N.J.) as a negative and positive control, respectively. Tumor size in each group was measured daily over a one week period. Both dosing regimens of PG-PTX were more efficient than ABRAXANE® in inhibiting tumor growth in comparison to the 'no drug' control (vehicle injections), indicating that pharmacologically active paclitaxel was regenerated from the prodrug construct at therapeutically adequate levels over time. No visible toxicity associated with the treatment was observed in the animals administered with PG-PTX at either dosing regimen. FIG. 5 shows the resulting tumor volumes as a function of time.

Example 17

Figure 6:
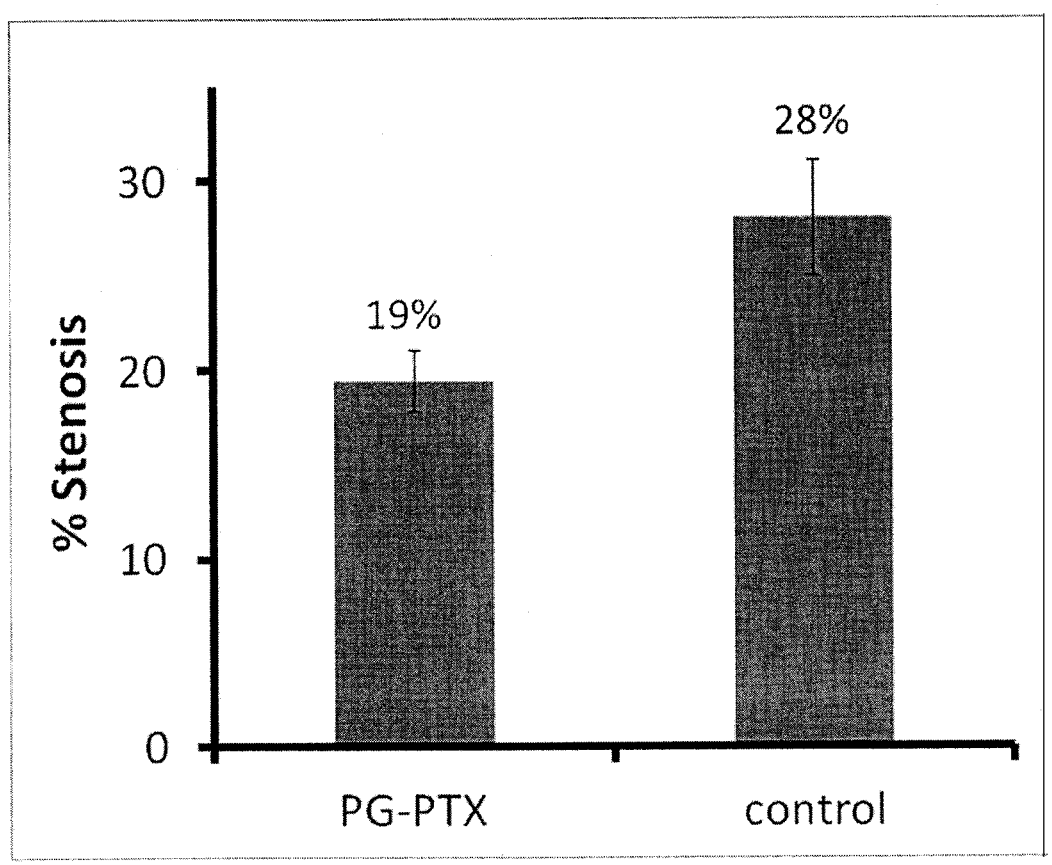
FIG. 6 shows % stenosis as a measure of vessel reobstruction in the rat carotid model of in-stent restenosis, using a rapidly cleavable polyglutamate-based paclitaxel prodrug according to the invention vs. a control.

Antirestenotic Effect of poly-L-glutamate Based PTX Prodrug in the Rat Carotid Model of In-Stent Restenosis The formulation of PG-PTX was prepared according to the method described in Example 5. Under general anesthesia the left common carotid artery of male Sprague-Dawley rats (450-500 g) were injured by four passages of a Fogarty catheter before deployment of a 304-grade stainless steel stent. A catheter was introduced via the external carotid into the common carotid artery and positioned distal to the stent. A 15-mm segment of the common carotid artery encompassing the site of stent placement was then isolated by ligatures, the PG-PTX formulation was applied at an estimated dose of 15 μL over 1 minute, and excess was evacuated. The ligatures were then released. Rats were euthanized 14 days after treatment. The stented carotid arteries were processed for morphometric measurements carried out in a blinded fashion in comparison to a 'stenting only' control group (n=7 and 6, respectively). The extent of in-stent restenosis was reduced in the PG-PTX group in comparison to control animals, with the difference in % stenosis (19±2% vs. 28±3%, respectively) reaching a statistically significant level (p=0.035, Mann-Whitney Rank Sum Test). FIG. 6 shows these results graphically.

The described methods and compositions may permit efficient delivery of chemically labile drugs, such as PTX, protected from degradation and inactivation by entrapment in nanoparticles in a form that does not exhibit premature escape from the carrier. They may also enable the protracted release of the in situ activatable prodrug compound from the carrier in a way that can be better adjusted to therapeutic uses than the relatively rapid release characterizing the unmodified drug compound, thereby diminishing adverse effects caused by drug redistribution to non-target tissues.

What is claimed is:

1. A system comprising a plurality of magnetic nanoparticles comprising a prodrug according to formula (I), an implantable medical device, and a source of uniform magnetic field capable of producing temporary magnetization of the implantable medical device and/or the magnetic nanoparticles,

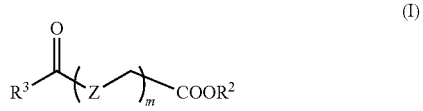

(I)

wherein $R^2$ is a residue of a drug, said drug having a hydroxyl group by which the $COOR^2$ group is formed; Z is O; m is 0 or 1; and $R^3$ is an organic moiety comprising a lipophilic group or a residue of a polymer.

2. The system according to claim 1, wherein $R^3$—CO is a residue of a carboxylic acid having from 8 to 30 carbon atoms.

3. The system according to claim 1, wherein $R^3$—CO is a residue of a carboxylic acid selected from the group consisting of palmitic acid, stearic acid, oleic acid, ricinoleic acid, docosahexaenoic acid and retinoic acid.

4. The system according to claim 1, wherein $R^3$ comprises a cholesterol or tocopherol moiety.

* * * * *